United States Patent [19]

Niewöhner et al.

[11] Patent Number: 5,191,092

[45] Date of Patent: Mar. 2, 1993

[54] ANTITHROMBOTIC ISO- AND HETEROCYCLIC PHENYLSULPHONAMIDES

[75] Inventors: Ulrich Niewöhner, Wermelskirchen; Franz-Peter Hoever, Cologne; Elisabeth Perzborn, Wuppertal; Volker-Bernd Fiedler, Leverkusen, all of Fed. Rep. of Germany; Peter Norma, Berks, United Kingdom; Hilary P. Francis, Berks, United Kingdom; Marie G. McKenniff, Berks, United Kingdom

[73] Assignee: Bayer Aktiengesellschaft, Leverkusen, Fed. Rep. of Germany

[21] Appl. No.: 588,793

[22] Filed: Sep. 26, 1990

[30] Foreign Application Priority Data

Nov. 2, 1989 [GB] United Kingdom ............... 8924755

[51] Int. Cl.$^5$ ................ C07D 311/92; C07D 311/78
[52] U.S. Cl. ................................. 549/385; 549/389
[58] Field of Search .............. 549/394, 389, 385, 395; 514/454

[56] References Cited

U.S. PATENT DOCUMENTS 4,882,353  11/1989  Niewöhner et al. ............... 514/456

FOREIGN PATENT DOCUMENTS 0253257  1/1988  European Pat. Off. .
0270929  6/1988  European Pat. Off. .
0315009  5/1989  European Pat. Off. .

OTHER PUBLICATIONS

Niewoehner et al., CA., 111, 232575e, 1989 (Abstract of EP 315,009).

Primary Examiner—Nicky Chan
Attorney, Agent, or Firm—Sprung Horn Kramer & Woods

[57] ABSTRACT

Iso- and heterocyclic phenylsulphonamides can be prepared by reaction of corresponding iso- and heterocyclic amines with phenylsulphonic acid derivatives. The iso- and heterocyclic phenylsulphonamides have thrombocyte aggregation-inhibiting and thromboxane $A_2$ antagonist action and can be used in medicaments.

7 Claims, No Drawings

ANTITHROMBOTIC ISO- AND HETEROCYCLIC PHENYLSULPHONAMIDES

The invention relates to iso- and heterocyclic phenyl-sulphonamides, to a process for their preparation and to their use in medicaments, in particular as antithrombotics.

It is already known that some chroman derivatives have a hypotensive action [compare DE-OS (German Published Specification) 3,411,993]. In addition, substituted aminomethyl-5,6,7,8-tetrahydronaphthyl-oxyacetic acids having an antithrombotic, antiatherosclerotic and antiischaemic action are described in DE-A1 3,642,105. Furthermore, bicyclic chroman derivatives having thrombocyte aggregation-inhibiting action are described in DOS 3,737,195.

Thrombosis and arteriosclerotic vascular changes are controlled in particular by the metabolism of two metabolites of arachidonic acid, namely thromboxane $A_2$ (TXA$_2$) and prostacyclin (PGI$_2$). TXA$_2$ has an aggregating effect on the blood platelets and PGI$_2$ has an antiaggregating effect. Moreover, TXA$_2$ acts as a vasoconstrictor and bronchoconstrictor and PGI$_2$ as a vasodilator and bronchodilator.

In a number of thromboembolic and ischaemic disorders, hyperaggregability of the platelets or elevated platelet consumption leads to an increased thromboxane synthesis, so that the TXA$_2$ and PGI$_2$ equilibrium is disturbed. It is therefore desirable for the therapy and prophylaxis of thromboembolic and ischaemic disorders to inhibit the effect of thromboxane and thus to increase the protective property of PGI$_2$.

The invention relates to iso- and heterocyclic phenyl-sulphonamides of the general formula (I)

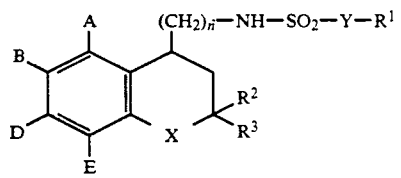

in which

A, B, D and E are identical or different and represent hydrogen, hydroxyl, halogen, trifluoromethyl, trifluoromethoxy, straight-chain or branched alkyl or alkoxy in each case having up to 8 carbon atoms, or represent aryl having 6 to 10 carbon atoms, which is optionally monosubstituted to trisubstituted by identical or different substituents from the series comprising halogen, trifluoromethyl, trifluoromethoxy, carboxyl, nitro, cyano or by straight-chain or branched alkyl, alkoxy or alkoxycarbonyl in each case having up to 8 carbon atoms, or represent a group of the formula —(CH$_2$)$_m$—CO—Z or —O—(CH$_2$)$_p$—CO—Z, wherein m—denotes a number 0, 1, 2, 3 or 4, p—denotes a number 1, 2, 3 or 4, and Z—denotes hydroxyl, straight-chain or branched alkoxy having up to 8 carbon atoms, aryloxy having 6 to 10 carbon atoms or a group of the formula —NR$^4$R$^5$, wherein, R$^4$ and R$^5$ are identical or different and denote hydrogen, straight-chain or branched alkyl having up to 8 carbon atoms or aryl having 6 to 10 carbon atoms, with the proviso that either A and B or B and D or D and E together must form a 5- to 7-membered saturated or unsaturated carbocycle fused to the basic structure or a heterocycle having up to 4 heteroatoms from the series comprising nitrogen, oxygen, sulphur or a group —NR$^6$, wherein R$^6$—denotes hydrogen, straight-chain or branched alkyl having up to 8 carbon atoms, aryl having 6 to 10 carbon atoms or a group of the formula —(CH$_2$)$_p$—CO—Z, wherein p and Z have the abovementioned meanings, and which in turn may be substituted by a group of the formula —(CH$_2$)$_m$—CO—Z or —O—(CH$_2$)$_p$—CO—Z, wherein m, p and Z have the abovementioned meanings, Y—represents the group —(CH$_2$)$_s$—, wherein s—denotes a number 0, 1, 2, 3 or 4, R$^1$—represents aryl having 6 to 10 carbon atoms, which is optionally monosubstituted to pentasubstituted by identical or different substituents from the series comprising halogen, cyano, nitro, trifluoromethyl, difluoromethyl, difluoromethoxy, trifluoromethoxy, carboxyl, aryloxy having 6 to 10 carbon atoms, by straight-chain or branched alkyl, alkoxy or alkoxycarbonyl in each case having up to 8 carbon atoms or by the group —NR$^4$R$^5$, wherein R$^4$ and R$^5$ have the abovementioned meanings, n—represents a number 0, 1 or 2, R$^2$ and R$^3$ are identical or different and represent hydrogen, straight-chain or branched alkyl or alkoxy in each case having up to 8 carbon atoms, represent a group of the formula —(CH$_2$)$_m$—CO—Z or —NR$^4$R$^5$, wherein m, Z, R$^4$ and R$^5$ have the abovementioned meanings, X—represents oxygen or the —CH$_2$— group, and their salts The substances according to the invention surprisingly show a good thrombocyte aggregation-inhibiting action and can be used for the treatment of thromboembolic disorders. Furthermore, they can be used for the treatment of asthma.

In the context of the present invention, physiologically acceptable salts are preferred. Physiologically acceptable salts of the iso- and heterocyclic phenylsulphonamides can be salts of the substances according to the invention with bases. In general, salts with inorganic or organic bases may be mentioned here.

Salts in the context of the present invention are additionally salts of the univalent metals such as alkali metals and the ammonium salts. Sodium salts, potassium salts, ammonium salts and the triethylammonium salt are preferred.

The compounds according to the invention exist in stereoisomeric forms which either behave as image and mirror image (enantiomers) or which do not behave as image and mirror image (diastereomers). The invention relates both to the antipodes and to the racemates as well as to the mixtures of diastereomers. The racemates, just as the diastereomers, can be separated into the stereoisomerically uniform constituents in a known manner (cf. E. L. Eliel, Stereochemistry of Carbon Compounds, McGraw Hill, 1962).

The following isomeric forms of the iso- and heterocyclic substituted phenylsulphonamides and may be mentioned as examples.

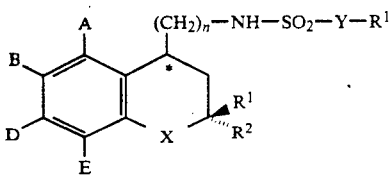

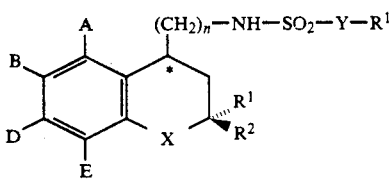

Preferred compounds of the general formula (I) are those in which

A, B, D and E are identical or different and represent hydrogen, hydroxyl, fluorine, chlorine, bromine, trifluoromethyl, trifluoromethoxy, straight-chain or branched alkyl or alkoxy in each case having up to 6 carbon atoms, or represent a group of the formula $—(CH_2)_m—CO—Z$ or $—O—(CH_2)_p—CO—Z$, wherein m—denotes a number 0, 1, 2 or 3, p—denotes a number 1, 2 or 3, and Z—denotes hydroxyl, straight-chain or branched alkoxy having up to 6 carbon atoms or phenoxy, with the proviso that either A and B or B and D or D and E together form a cyclopentano, cyclohexano, benzo, pyrrolidinyl, imidazolyl, pyrrolyl, piperazinyl, 1,4-oxazirano, furanoyl or tetrahydrofurano ring fused to the basic structure, which may in turn be substituted by a group of the formula $—(CH_2)_m—CO—Z$ or $—O—(CH_2)_p—CO—Z$ wherein m, p and Z have the abovementioned meanings, Y—represents the group $—(CH_2)_s—$, wherein s—denotes a number 0, 1, 2 or 3, $R^1$—represents phenyl which is optionally monosubstituted to tetrasubstituted by identical or different substituents from the series comprising phenoxy, fluorine, chlorine, bromine, iodine, cyano, nitro, trifluoromethyl, trifluoromethoxy, difluoromethoxy, difluoromethyl, carboxyl, or by straight-chain or branched alkyl or alkoxy in each case having up to 6 carbon atoms, n—represents a number 0 or 1, $R^2$ and $R^3$ are identical or different and represent hydrogen, straight-chain or branched alkyl or alkoxy in each case having up to 6 carbon atoms, or represent a group of the formula $—(CH_2)_m—CO—Z$ or $—NR^4R^5$, wherein m, Z, $R^4$ and $R^5$ have the abovementioned meanings, and X—represents oxygen or the $—CH_2—$ group, and their salts.

Particularly preferred compounds of the general formula (I) are those in which

A, B, D and E are identical or different and represent hydrogen, hydroxyl, fluorine, chlorine, trifluoromethyl or trifluoromethoxy, or represent a group of the formula $—(CH_2)_m—CO—Z$ or $—O—(CH_2)_p—CO—Z$, wherein m—denotes a number 0, 1 or 2, p—denotes a number 1 or 2 and Z—denotes hydroxyl, straight-chain or branched alkoxy having up to 4 carbon atoms or phenoxy, with the proviso that either A and B or B and D or D and E together form a cyclopentano, cyclohexano, benzo or tetrahydrofurano ring fused to the basic structure, which may in turn be substituted by a group of the formula $—(CH_2)_m—CO—Z$ or $—O—(CH_2)_p—CO—Z$, wherein m, p and Z have the abovementioned meanings, Y—represents the group $—(CH_2)_s—$, wherein s—denotes the number 0 or 1, $R^1$—represents phenyl which is optionally monosubstituted to trisubstituted by identical or different substituents from the series comprising phenoxy, cyano, fluorine, chlorine, trifluoromethyl, trifluoromethoxy, difluoromethyl, difluoromethoxy, nitro, carboxyl or by straight-chain or branched alkyl or alkoxy having up to 4 carbon atoms, n—represents the number 1, $R^2$ and $R^3$ are identical or different and represent hydrogen or straight-chain or branched alkyl having up to 4 carbon atoms and X—represents oxygen or the $—CH_2—$ group, and their salts.

In addition, a process for the preparation of the compounds of the general formula (I) according to the invention

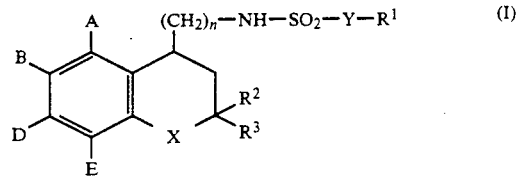

in which A, B, D, E, n, X, Y, $R^1$, $R^2$ and $R^3$ have the abovementioned meanings, has been found, which is characterized in that amines of the general formula (II)

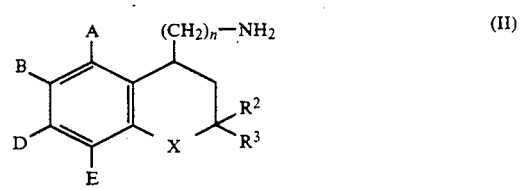

in which A, B, D, E, n, X, $R^2$ and $R^3$ have the abovementioned meanings, are sulphonated with sulphonyl compounds of the general formula (III)

in which $R^1$ and Y have the abovementioned meanings and

W—represents fluorine, chlorine, bromine or hydroxyl, in inert solvents, if appropriate in the presence of an acid-binding agent, and in the case in which one or more of the abovementioned radicals A, B, D, E, $R^2$ and/or $R^3$ represent esters or amides, hydrolyzed to give the corresponding acids.

The process according to the invention can be illustrated by the following reaction scheme:

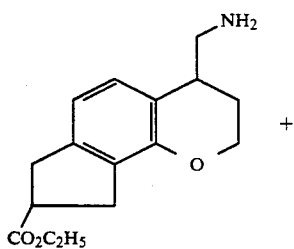

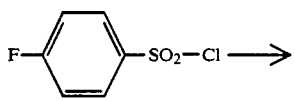

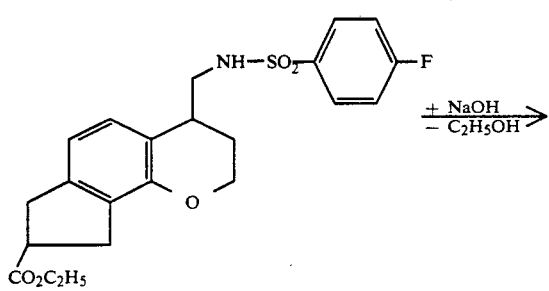

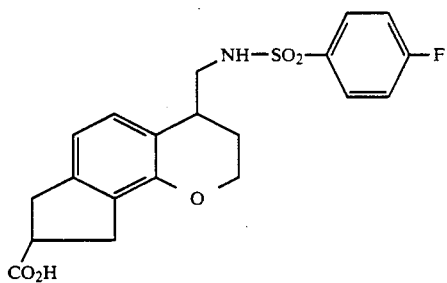

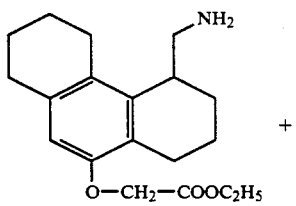

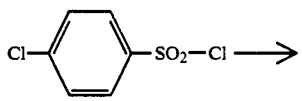

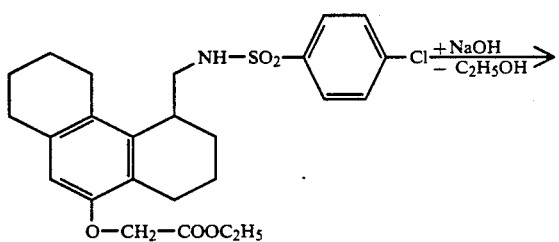

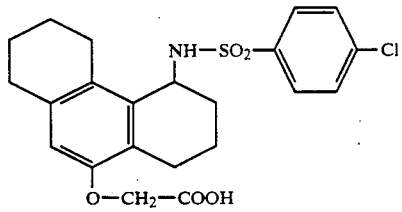

Suitable solvents for the sulphonation are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Tetrahydrofuran is particularly preferred.

The sulphonation is in general carried out in a temperature range from $-80°$ C. to $+150°$ C., preferably from $0°$ C. to $+80°$ C.

The sulphonation is in general carried out at normal pressure. However, it is also possible to carry out the process at elevated pressure or at reduced pressure (for example in a range from 0.5 to 5 bar).

In general, 1 to 3 moles, preferably 1 to 2 moles, particularly preferably 1 mole of sulphonyl compound (III) is employed, relative to 1 mole of the amine.

The sulphonic acids and their activated derivatives of the general formula (III) are known or can be prepared by known methods [cf. Houben-Weyl's, "Methoden der organischen Chemie" (Methods of Organic Chemistry), volume IX, p. 407 et seq.].

Acid-binding agents which can be employed for the sulphonation are alkali metal or alkaline earth metal carbonates such as sodium carbonate, potassium carbonate, alkali metal or alkaline earth metal hydroxides, such as, for example, sodium hydroxide or potassium hydroxide, or organic bases such as pyridine, triethylamine, N-methylpyridine, or bicyclic amidines such as 1,5-diazabicyclo[3.4.0]non-5-ene (DBN) or 1,5-diazabicyclo[5.4.0]undec-5-ene (DBU). Potassium carbonate is preferred.

The acid-binding agents are in general employed in an amount from 0.5 to 3 moles, preferably from 1 to 1.5 moles, relative to the compounds of the general formula (III).

The hydrolysis of the carboxylic acid esters is carried out by customary methods, by treating the esters with customary bases in inert solvents, it being possible to convert the initially formed salts into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogencarbonate, or alkali metal alkoxides such as sodium ethoxide, sodium methoxide, potassium ethoxide, potassium methoxide or potassium tert. butoxide.

Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to use mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 moles, preferably from 1 to 1.5 moles, relative to 1 mole of the ester. Molar amounts of the reactants are particularly preferably used.

The amines of the general formula (II)

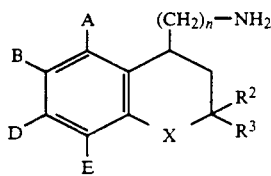

(IIa)

in which

A, B, D, E, X, $R^2$ and $R^3$ have the abovementioned meanings and n represents the number 1 or 2, are new and can be prepared by reacting ketones of the general formula (IV)

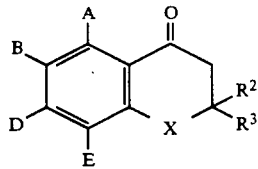

(IV)

in which A, B, D, E, X, $R^2$ and $R^3$ have the abovementioned meanings, first with trimethylsilyl cyanide of the formula (V)

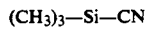

$(CH_3)_3-Si-CN$ (V)

in inert solvents, if appropriate in the presence of a catalyst such as, for example, Lewis acids, bases or crown ethers, with alkali metal cyanides, such as, for example, sodium cyanide via the corresponding silylated cyanohydrin step by treatment with acids to give the $\alpha,\beta$-unsaturated nitriles of the general formula (VI)

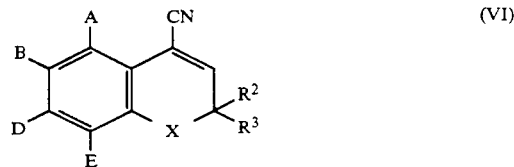

(VI)

in which A, B, D, E, X, $R^2$ and $R^3$ have the abovementioned meanings, and in a further step, reducing both the double bond and the cyano group, either simultaneously or in a two-step reaction, by catalytic hydrogenation, if appropriate in the presence of ammonia in inert solvents.

The compounds of the general formula (IIb), in which A, B, D, E, X, $R^2$ and $R^3$ have the abovementioned meanings and n represents the number 0, are also new and can be prepared from the compounds of the general formula (IV) by catalytic reductive amination in analogy to processes known from the literature [cf. J. Am. Chem. Soc. 93, 2897 (1971); Rylander, "Catalytic Hydrogenation", p. 291-303, Academic Press, New York, 1967; Org. Reactions 4, 174-255 (1948)] or by reductive amination using complex metal hydrides [cf. Harada, in Patai, "The Chemistry of the Carbon-Nitrogen-Double Bond, "Interscience Publishers, New York, 1970, p. 276-293; J. Am. Chem. Soc., 93, 2837 (1971)].

Suitable catalysts for the reaction with trimethylsilyl cyanide are the customary Lewis acids, such as, for example, aluminum trichloride, boron trifluoride etherate, zinc iodide, tin tetrachloride, or organic bases such as pyridine or triethylamine, or crown ether complexes, such as, for example, 18-crown-6 x KCN. Boron trifluoride etherate and zinc iodide are preferred. The reaction can optionally also be carried out without catalyst.

In the reaction, the catalyst is in general employed in an amount from 0.1 to 5 moles, preferably from 1 to 3 moles, relative to 1 mole of the compound of the formula (V).

The reaction is carried out in one of the above-mentioned inert solvents, such as, for example, ethers, halogenated hydrocarbons or toluene, preferably in diethyl ether, tetrahydrofuran, methylene chloride or toluene. The reaction can also be carried out without solvent.

The reaction temperature is between 0° C. and +130° C., preferably at +20° C. to +80° C.

Suitable acids for the conversion of the crude silylated cyanohydrins into the $\alpha, \beta$-unsaturated nitriles (VI) are organic acids such as trifluoroacetic acid, p-toluenesulphonic acid, formic acid, acetic acid, or mineral acids such as, for example, hydrochloric acid, sulphuric acid or nitric acid.

Suitable solvents are alcohols such as methanol, ethanol, propanol, or chlorinated hydrocarbons such as methylene chloride, or ethers such as tetrahydrofuran, or dimethylformamide, benzene or toluene. It is additionally possible to work without solvents.

The reaction is in general carried out in a temperature range from 0° C. to +120° C., preferably at +25° C. to +40° C.

The reduction of the double bond by hydrogenation is in general carried out using hydrogen in the presence of a catalyst such as, for example, platinum or platinum oxides, rhodium, ruthenium, chlorotris(triphenylphosphine)rhodium, or palladium on animal carbon, preferably using palladium on animal carbon in a temperature range from 0° C. to +150° C., preferably from +25° C. to +100° C.

The reduction of the nitrile group to the amino group is in general carried out using metal hydrides, such as, for example, aluminum hydride or its mixtures, in a temperature range from −20° C. to +150° C., preferably from 0° C. to +100° C. or by hydrogenation in the presence of a noble metal catalyst such as platinum, palladium, palladium on animal carbon or Raney nickel, in a temperature range from 0° C. to +100° C.

Suitable solvents are protic solvents such as, for example, methanol, ethanol and/or aprotic solvents such as, for example, tetrahydrofuran, toluene, dimethylformamide, methylene chloride or dioxane, to which, if appropriate, liquid ammonia is added.

The hydrogenation is carried out a pressure of 4 to 300 atm, preferably 50 to 150 atm.

The amount of catalyst employed is 0.5 to 5, preferably 1 to 1.5 mole %, relative to the compound of the general formula (VI).

When carrying out the reduction in a two-step reaction, the reduction of the double bond takes place first and then the reduction of the nitrile group to the amino group in the abovementioned manner. However, it is also possible to carry out the reduction of the double bond and the nitrile group in one step by choosing the reaction conditions for the abovementioned reduction of the nitrile group (higher pressure). Reduction via a two-step reaction is preferred. In addition, it is possible to carry out the hydrogenation by other customary methods [cf. Rylander, "Catalytic Hydrogenation", Academic Press, Inc. New York (1967)].

The trimethylsilyl cyanide of the general formula (V) is known [cf. J. Am. Chem. Soc. 80, 4151–4153 (1958); D. A. Evans, G. L. Carrol, L. H. Truesdale, J. Org Chem. 39, 914 (1974)].

The reductive amination takes place in one of the abovementioned solvents, preferably in methanol, ethanol, propanol, diethyl ether, tetrahydrofuran, dioxane, chloroform, acetonitrile, dimethylformamide, glacial acetic acid or mixtures thereof.

Suitable reducing agents are the customary complex hydrides, such as, for example, sodium borohydride, sodium cyanoborohydride, or aminoborane complexes or hydrogen, if appropriate in the presence of a metal catalyst such as, for example, Raney nickel or palladium.

Ammonium-containing components which are employed are aqueous ammonia solution, gaseous ammonia, and also ammonium salts such as ammonium chloride, ammonium sulphate, ammonium acetate or ammonium formate.

The reaction can be carried out at normal or elevated pressure (1.0 to 5 bar). In general, the reaction is carried out at normal pressure when using complex metal hydrides and at elevated pressure when using hydrogen.

The reductive amination is generally carried out in a temperature range from +10° C. to +120° C.

Some of the compounds of the general formula (IV) are known [cf. K. Yamamoto, H. Takushima, H. Yumiaha, H. Nagazuki, Bull. Chem. Soc. Jap. 58 (1985), 12, 3633–3638; J. Med. Chem. 20 (5), 664–669; DE 253,688; Chem. Pharm. Bull. 29 (11), 3232–3237; J. Am. Chem. Soc. 110 (9), 2919–2924; J. Org. Chem. 53 (19), 4515–4519; J. Org. Chem. 50 (14), 2435–2438; Brit. GB 1,077,066; J. Prakt. Chem. 314 (5-6), 941–949; Liebigs Ann. Chem. (12), 2012–2030; Rev. Roum. Chim. (21), (11-12), 1543–1554; EP 150,966 A2; Indian J. Chem. Sect. B, 26B (8), 786–787], or they can be prepared by reacting hydroxy compounds of the general formula (VII)

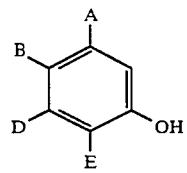

(VII)

in which
A, B, D and E have the abovementioned meanings,
a) according to methods known from the literature either with acrylonitrile or acryloyl chlorides, if appropriate in the presence of a phase transfer catalyst, such as, for example, triethylbenzylammonium hydroxide or trimethylbenzylammonium hydroxide, in one of the abovementioned inert aprotic solvents to give compounds of the general formula (VIII)

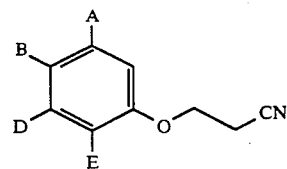

(VIII)

in which A, B, D and E have the abovementioned meanings, and subsequently cyclizing under Friedel-Crafts conditions, for example in the presence of hydrofluoric acid, or
b) first reacting, for example, with propargyl bromide, then brominating by methods known from the literature, for example with NBS/AgNO₃ and cyclizing with mercury complexes, such as, for example, mercury(II) trifluoroacetate, or by cyclizing
c) compounds of the general formula (IX) (with X=CH₂)

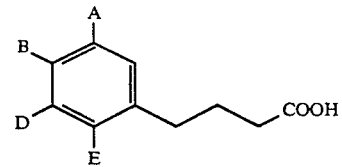

(IX)

in which A, B, D and E have the abovementioned meanings, by the known abovementioned methods, for example with polyphosphoric acid or hydrofluoric acid [cf. J. M. Lockhart in Ellis "Chromenes, Chromanones and Chromones", Interscience Publication, New York, 1977, page 236–237, p. 237–256], it being possible to introduce the radicals of the formula —(CH₂)$_m$—CO—Z or —O—(CH₂)$_p$—CO—Z, if they have not already been carried along by the corresponding substituted starting compounds, if appropriate by alkylation, for example, of the compounds of the general formulae (II), (IV) or (VI), in which one of the radicals A, B, D or E denotes a hydroxyl group, with carboxylic acid derivatives of the formulae

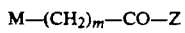  (X)

or

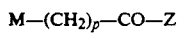  (XI)

in which m, p and Z have the abovementioned meanings and

M—denotes a leaving group such as, for example, Cl, Br, I, —O—SO$_2$CH$_3$ or —O—SO$_2$—C$_6$H$_4$—p—CH$_3$, by methods known from the literature [cf. Patai "The Chemistry of the Hydroxyl Group", pt. 1, p. 454-466, Interscience Publishers, New York, 1971, Tetrahedron 30, 1379 (1974)].

The reaction with acrylonitrile and with acryloyl chlorides take place in a temperature range from 0° C. to +160° C., preferably at +80° C. to +110° C. at normal pressure.

The compounds of the general formula (VII) are known per se or can be prepared by known methods [cf. S. C. Lahiri, J. K. Gupta, J. Indian Chem. Soc. 53 (1976), 1041; A. Mukkopadhyay, A. Roy, S. C. Lahiri, J. Indian Chem. Soc. 62 (1985), 690–692; H. O. House, C. B. Hudson, J. Org. Chem. 35 (1970) 3, 647–651; H. Immer, J. F. Baghi, J. Org. Chem. 33 (6), 1968, 2457; L. N. Monder, S. G. Pyne, Australian J. Chem. 1981, 34, 1899-1911; H. Immer, J. F. Baghi, J. Org. Chem. 33 (6), 1968, 2457; C. Goldenberg, R. Wanderstrick, F. Binen, R. Charlier, Chim. Ther. 8(3), 1973, 259].

The compounds of the general formulae (VIII) and (IX) are known per se or can be prepared by known methods [cf. R. B. Burtner, J. M. Brown, J. Am. Chem. Soc. 73 (1951), 897; W. J. Awaward, F. G. Baddar, A. E. Marei, J. Chem. Soc. 1954, 4538-4541].

The compounds of the general formula (X) and (XI) are known or can be prepared by customary methods [cf. Beilstein 3, 5; Fieser 1, 247; 2, 129; 3, 95; 5, 213].

The iso- and heterocyclic phenylsulphonamides or their salts according to the invention can be employed as active compounds in medicaments. The active compounds have a strong thrombocyte aggregation-inhibiting and thromboxane A$_2$ antagonist action. They can preferably be employed for the treatment of thromboses, thromboembolisms, ischaemias, as antiasthmatics and as antiallergics.

The iso- and heterocyclic phenylsulphonamides according to the invention can be used both in human medicine and in veterinary medicine.

The active compounds according to the invention can be converted in a manner known per se using inert non-toxic, pharmaceutically suitable excipients or solvents into the customary formulations, such as tablets, capsules, coated tablets, pills, granules, aerosols, syrups, emulsions, suspensions and solutions. In this connection, the therapeutically active compound should in each case be present in a concentration from about 0.5 to 90% by weight, preferably from 5 to 70% by weight, relative to the preparation, which is sufficient in order to achieve the dosage range indicated.

USE EXAMPLE

In order to determine the thrombocyte aggregation-inhibiting action, blood from healthy subjects of both sexes was used. One part of 3.8% strength aqueous sodium citrate solution was added to 9 parts of blood as an anticoagulant. Platelet-rich citrate plasma (PRP) was obtained from this blood by means of centrifugation (Jürgens/Beller, Klinische Methoden der Blutgerinnungsanalyse (Clinical Methods of Blood Coagulation Analysis); Thieme Verlag, Stuttgart, 1959).

For these investigations 0.8 ml of PRP and 0.1 ml of the active compound solution were preincubated at 37° C. in a waterbath. The thrombocyte aggregation was then determined at 37° C. in an aggregometer (Therapeutische Berichte 47, 80-86, 1975) by the turbidometric method (Born G.V.R., J. Physiol. (London), 162, 67, 1962). For this purpose, 0.1 ml of collagen, an aggregation-inducing agent, was added to the preincubated sample. The change of the optical density in the sample of PRP was recorded for a period of 6 minutes and the aggregation was determined after 6 minutes. For this purpose, the percentage inhibition compared to the control is calculated. The threshold concentration is indicated by the range of the minimum effective concentration.

The threshold concentrations are between 0.003-10 mg/l, for example compound of Example 73. EC=0.03-0.01 mg/l.

The formulations are prepared, for example, by extending the active compounds with solvents and/or excipients, if appropriate using emulsifiers and/or dispersants, it being possible, for example, in the case of the use of water as a diluent, to use organic solvents as auxiliary solvents if appropriate.

Auxiliaries which may be mentioned are, for example: water, non-toxic organic solvents such as paraffins (for example mineral oil fractions), vegetable oils (for example groundnut/sesame oil), alcohols (for example ethyl alcohol, glycerol), glycols (for example propylene glycol, ethylene glycol), solid excipients, such as, for example, ground natural minerals (for example kaolins, clays, talc, chalk), ground synthetic minerals (for example highly disperse silicic acid, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin, sulphite waste liquors, methylcellulose, starch and polyvinylpyrrolidone) and lubricants (for example magnesium stearate, talc, stearic acid and sodium laurylsulphate).

Administration can take place in a customary manner, preferably orally or parenterally, in particular perlingually or intravenously. In the case of oral administration, tablets may of course also contain additions, such as sodium citrates, calcium carbonate and dicalcium phosphate together with various additives, such as starch, preferably potato starch, gelatin and the like in addition to the excipients mentioned. Furthermore, lubricants, such as magnesium stearate, sodium laurylsulphate and talc can additionally be used for tabletting. In the case of aqueous suspensions and/or elixirs which are intended for oral administration, various flavor enhancers or colorants may also be added to the active compounds in addition to the abovementioned auxiliaries.

In the case of parenteral administration, solutions of the active compounds can be employed using suitable liquid excipients.

In general, it has proved advantageous on intravenous administration to administer amounts of about 0.001 to 1 mg/kg, preferably about 0.01 to 0.5 mg/kg of body weight to attain effective results. On oral administration, the dosage is in general about 0.01 to 20 mg/kg, preferably 0.1 to 10 mg/kg of body weight.

However, it may be advantageous to deviate from the amounts mentioned, depending on the body weight or the type of application route, on individual behavior towards the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of larger amounts, it may be advisable to divide these into a number of individual doses over the day.

PREPARATION EXAMPLES

A) STARTING COMPOUNDS

Example 1

4-(1-Methoxy-5,6,7,8-tetrahydro-2-naphthyl)-butyric acid

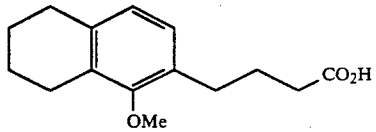

42 g (0.15 mol) of 3-(1-methoxy-2-naphthoyl)propionic acid [cf. W. I. Awad, F. G. Badder, A. E. Marei, J. Chem. Soc. 1954, p. 4538] are hydrogenated for 6 h at 60° C. and 30 bar of hydrogen in 800 ml of ethanol in the presence of 12 g of palladium/animal carbon (10% strength) as a catalyst. The catalyst is filtered off, the solution is evaporated and the residue is flash chromatographed on silica gel using methylene chloride/methanol 10:1 as the eluent.

Yield: 28.1 g (69.4% of theory).

M.p.: 67° C. (not recrystallized, solid after chromatography).

Example 2

4-(1-Methoxy-2-naphthyl)butyric acid

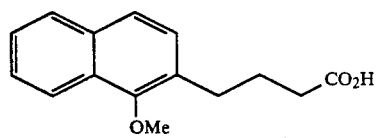

155.4 g of zinc turnings, 18.6 g of mercury(II) chloride, 231.2 ml of water and 7.7 ml of concentrated hydrochloric acid are combined and shaken well for 5 minutes. The aqueous phase is decanted off from the zinc amalgam and the latter is added to a solution of 78.45 g (0.31 mol) of the compound from Example 1 in 140 ml of toluene, 175 ml of water, 310 ml of concentrated hydrochloric acid and 15 ml of glacial acetic acid. The mixture is heated to reflux for 18 h, 81 ml of concentrated hydrochloric acid being added every 6 h. The solution is filtered, shaken 3 times with 300 ml of ethyl acetate each time and the combined ethyl acetate phases are washed with 500 ml of saturated sodium chloride solution. After drying over sodium sulphate, the solution is evaporated and the residue is flash chromatographed on silica gel using $CH_2Cl_2$/acetone as the eluent.

Yield: 57.74 g (77.5% of theory).

$^1$H-NMR (CDCl$_3$): δ=2.05 (quintet, 2H); 2.4 (t, 2H); 2.85 (t, 2H); 3.9 (s, 3H); 7.3–7.6 (m, 4H); 7.8 (d, 1H; 8.16 (d, 1H).

Example 3

1,2,3,4,7,8-Hexahydro-9-methoxy-5(6H)-phenantrenone

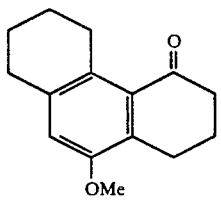

84.2 g (0.34 mol) of 4-(2-methoxy-5,6,7,8-tetrahydro-3-naphthyl)-butyric acid [cf. R. R. Burtner, J. M. Brown, J. Am. Chem. Soc. 73 (1951), 897] are added in portions at 100° C. to 1.362 kg of polyphosphoric acid. After 2 h at 100° C., 3 l of ice water are added to the cooled solution and the mixture is extracted 3 times using 500 ml of ethyl acetate each time. The combined ethyl acetate phases are dried over Na$_2$SO$_4$ and evaporated, and the residue is flash chromatographed on silica gel using petroleum ether/acetone 5:1 as the eluent.

Yield: 47.42 g (60.64% of theory).

$^1$H-NMR (CDCl$_3$): δ=1.65–1.8 (m, 4H); 2.05 (quintet, 2H); 2.6 (t, 2H); 2.75 (t, 2H); 2.85 (t, 2H); 3.05 (t, 2H); 3.8 (s, 3H); 6.7 (s, 1H).

Example 4

3,4,6,7,8,9-Hexahydro-5-methoxy-1(2H)-anthracenone

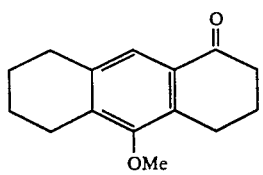

The title compound is obtained by reacting the compound from Example 1 in analogy to Example 3.

Yield: 79.9%.

$^1$H-NMR (CDCl$_3$): δ=1.75 (m, 4H); 2.1 (quintet, 2H); 2.6 (t, 2H); 2.8 (m, 4H); 2.9 (t, H); 3.75 (s, 3H); 7.6 (s, 1H).

Example 5

3,4-Dihydro-5-methoxy-1(2H)-anthracenone

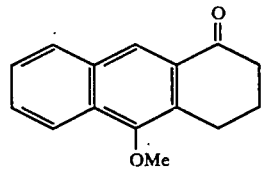

The title compound is obtained by reacting the compound from Example 2 in analogy to Example 3.

Yield: 52.1%.

$^1$H-NMR (CDCl$_3$): δ=2.15 (quintet, 2H); 2.78 (t, 2H); 3.15 (t, 2H); 3.9 (s, 3H); 7.4–7.65 (m, 2H); 7.95 (d, 1H); 8.1 (d, 1H); 8.45 (s, 1H).

Example 6

1,2,3,4,7,8-Hexahydro-9-hydroxy-5(6H)-phenanthrenone

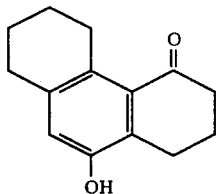

47.4 g (0.22 mol) of the 9-methoxy-phenanthrenone from Example 3 are dissolved in 605 ml of absolute methylene chloride and 440 ml of a 1 molar solution of boron tribromide in methylene chloride are added dropwise at −78° C. The mixture is stirred at −78° C. for 0.5 h, then at +20° C. for 3 h, cooled again to −78° C. and 620 ml of methanol is slowly added. The mixture is allowed to come to 20° C. and is evaporated. The residue is partitioned between 200 ml of $CH_2Cl_2$ and 200 ml of 1N NaOH solution, and the NaOH phase is separated and acidified to pH 1 using concentrated HCl solution with ice cooling. The precipitate is filtered off and dried in a high vacuum.

Yield: 40.66 g (91.3% of theory).
M.p.: 198° C.

Example 7

3,4,6,7,8,9-Hexahydro-5-hydroxy-1(2H)-anthracenone

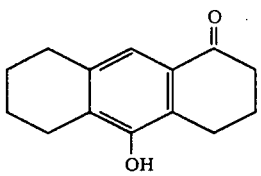

The compound from Example 4 is reacted analogously to Example 6.
Yield: 97.5%.
M.p.: 175–177° C. (from ligroin).

Example 8

3,4-Dihydro-5-hydroxy-1(2H)-anthracenone

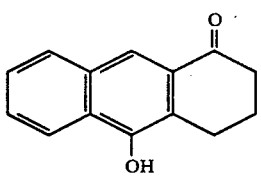

The compound from Example 5 is reacted analogously to Example 6.
Yield: 98.2%.
M.p.: 153–155° C. (not recrystallized, after chromatography).

Example 9

Ethyl (1,2,3,4,7,8-hexahydro-5(6H)-phenanthrenon-9-yl)oxyacetate

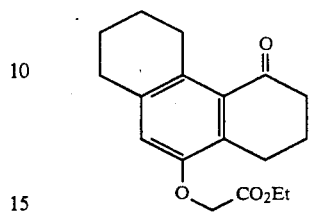

40.44 g (0.19 mol) of the compound from Example 6 is heated to reflux with 38.64 g (0.23 mol) of ethyl bromoacetate and 31.97 g (0.23 mol) of potassium carbonate in 190 ml of butanone for 5 h. After cooling, the precipitate is filtered off and washed well with acetone and the solution is evaporated. The residue is taken up in 100 ml of $CH_2Cl_2$, shaken 3 times with 50 ml of 10% strength NaOH solution each time, dried over $Na_2SO_4$ and evaporated. The residue is dried in a high vacuum.

Yield: 50.58 g (89.5% of theory).
M.p.: 70–75° C. (not recrystallized).

The compounds shown in Table 1 are prepared in analogy to the procedure of Example 9:

TABLE 1

| Example No. | Structure | Yield: |
|---|---|---|
| 10 | (phenanthrenone with O-CH2-CO2C2H5) | 74.9% |
| 11 | (hexahydroanthracenone with O-CH2-CO2C2H5) | 81.7% |
| 12 | (dihydroanthracenone with O-CH2-CO2C2H5) | 75.9% |

Example 13

Ethyl 5-methoxy-indan-2-carboxylate

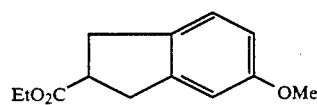

32.0 g (0.145 mol) of ethyl 6-methoxy-indan-1-one-2-carboxylate [cf. H. O. House, C. B. Hudson, J. Org. Chem. 35 (1970) 3, 647-651] are hydrogenated with 20 bar of $H_2$ at 50° C. for 5 h in 180 ml of MeOH in the presence of 5 g of palladium/carbon (5% strength) as a catalyst. The catalyst is filtered off, the methanol is stripped off in vacuo and the residue is distilled in a bulb tube furnace.

Yield: 21.93 g (68.7% of theory.
B.p.: 140-145° C. (0.15 mm bulb tube).

Example 14

5-Hydroxy-indan-2-carboxylic acid

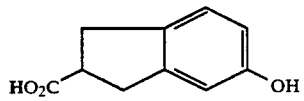

50 g (0.23 mol) of the compound from Example 13 are initially introduced in 780 ml of absolute $CH_2Cl_2$ at −78° C. 114 ml (1.2 mol) of boron tribromide in 360 ml of absolute $CH_2Cl_2$ are then added dropwise and the mixture is stirred at −78° C. for 30 minutes. It is then stirred at 0° C. for 2.5 h, subsequently cooled to −78° C. again and 690 ml of absolute MeOH are added cautiously. After 15 minutes, the mixture is evaporated, the residue is dissolved in 818 ml of MeOH, 272 ml of 2N NaOH solution are added and the mixture is stirred at 20° C. for 2 h. The methanol is evaporated in vacuo, the aqueous phase is washed with 200 ml of ethyl acetate and then acidified to pH 1-2 using concentrated hydrochloric acid with ice cooling. The aqueous phase is shaken twice with 100 ml of ethyl acetate each time, and the combined ethyl acetate phases are dried over $Na_2SO_4$ and evaporated. The residue is recrystallized from toluene.

Yield: 34 g (84% of theory).
M.p.: 179° C.

Example 15

2,2-Dimethyl-4-oxo-2,3,7,8-tetrahydro-7-carboxy-6H-cyclopenta[g]-1-benzopyran

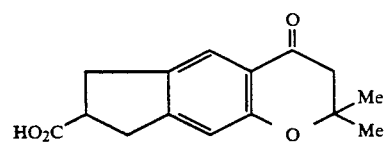

9.8 g (5.5 mmol) of 5-hydroxy-indan-2-carboxylic acid are dissolved in 20 ml of nitrobenzene and 20 ml of carbon disulphide and 16.12 g (121 mmol) of aluminum trichloride are added in portions. 7.8 g (66 mmol) of dimethylacryloyl chloride in 20 ml of nitrobenzene are then added dropwise and the mixture is heated to 90° C. for 3 h. After cooling, 40 ml of concentrated hydrochloric acid and 40 g of ice are added and the mixture is shaken twice with 100 ml of $CH_2Cl_2$ each time. The combined $CH_2Cl_2$ phases are evaporated, the nitrobenzene is distilled off in a water jet vacuum and the residue is taken up in 100 ml of 10% strength NaOH solution. The NaOH phase is shaken twice with 100 ml of $CH_2Cl_2$ each time, then acidified using concentrated HCl solution with ice cooling and extracted 3 times using 100 ml of $CH_2Cl_2$ each time. After drying over $Na_2SO_4$, the solution is evaporated and the residue is flash chromatographed on silica gel (eluent: $CH_2Cl_2$/acetone 10:1)

Yield: 5.01 g (35.3% of theory).
M.p.: 153° C. (not recrystallized).

The compounds shown in Table 2 were prepared in analogy to the procedure of Example 15:

TABLE 2

| Example No. | Structure | M.p. °C. |
|---|---|---|
| 16 | ![structure] | |
| 17 | ![structure] | 123-125 |
| 18 | ![structure] | 158 |
| 19 | ![structure] | 219 |

Example 20

Methyl 2,2-dimethyl-4-oxo-2,3,7,8-tetrahydro-6H-cyclopenta[g]-1-benzopyran-7-carboxylate

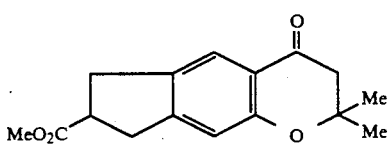

4.98 g (19.2 mmol) of the compound from Example 15 are dissolved in 38 ml of $CH_2Cl_2$ and 19 ml of absolute MeOH and 4.35 g (21.1 mmol) of dicyclohexylcarbodiimide and 20 ml of dimethylaminopyridine are added at 0° C. The mixture is allowed to come to room temperature and is stirred at 20° C. for 2 h. Precipitated dicyclohexylurea is filtered off and washed well with $CH_2Cl_2$, and the combined $CH_2Cl_2$ phases are washed twice with 1N NaOH solution, once with 1N hydrochloric acid and once with NaCl solution. After drying over $Na_2SO_4$, the solution is evaporated and the residue is flash chromatographed on silica gel (eluent: methylene chloride)

Yield: 3.79 g (72.2% of theory).

M.p.: 126° C. (after chromatography, not recrystallized).

The compounds shown in Table 3 were prepared in analogy to the procedure of Example 20.

TABLE 3

| Example No. | Structure | M.p. °C. |
|---|---|---|
| 21 | (indanone with CO₂CH₃ and CH₃/CH₃ dioxo side chain) | |
| 22 | (indanone with CH₂CO₂CH₃ and CH₃/CH₃ dioxo side chain) | 67 |
| 23 | (tetrahydronaphthalene with H₃CO₂C and CH₃/CH₃ dioxo side chain) | |
| 24 | (tetrahydronaphthalene with H₃CO₂C and CH₃/CH₃ dioxo side chain) | 118 |

Example 25

4-Fluoro-7-hydroxy-indan-1-one

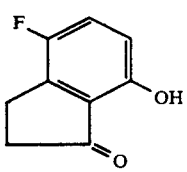

4-Fluoro-7-hydroxy-indan-1-one is prepared in analogy to the non-fluorinated compound by the process of S. Wagatsuma et al. [Org. Prep. Proced. Int., 5(2), 1973, 65–70] in two steps: 1. esterification of 4-fluorophenol and 3-chloropropionyl chloride by refluxing both components in toluene (yield: 86.1%, b.p: 150° C./30 mm); 2. heating the ester in the presence of AlCl₃ (yield: 53.9%, m.p.: 87° C.).

Example 26

Ethyl 4-fluoro-7-hydroxy-indan-1-one-2-carboxylate

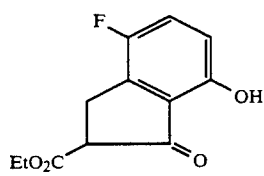

45 g (1.5 mmol) of sodium hydride (80%) and 88.5 g (0.75 mol) of diethyl carbonate are initially introduced in 375 ml of absolute tetrahydrofuran. 83 g (0.5 mol) of the indanone from Example 25 in 375 ml of absolute tetrahydrofuran are added dropwise at 20° C. and the mixture is refluxed for 3 h. After cooling, 360 ml of glacial acetic acid are added dropwise, 500 ml of CH₂Cl₂ and 500 ml of H₂O are added and the CH₂Cl₂ phase is separated. After washing the CH₂Cl₂ phase with saturated NaCl solution, the solution is dried over Na₂SO₄ and evaporated. The residue is recrystallized from ligroin.

Yield: 94.45 g (79.4% of theory).

M.p.: 77° C.

Example 27

Ethyl 7-hydroxy-indan-1-one-2-carboxylate

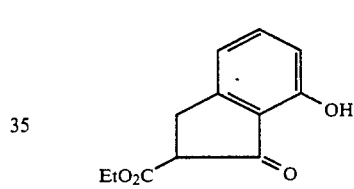

Analogously to the procedure for Example 26, the title compound was prepared from the known 7-hydroxyindan-1-one [cf. S. Wagatsuma et al., Org. Prep. Proced. Int. 5(2), 1973, 65–70].

Yield: 89.4%.

B.p.: 170° C./0.25 mm (bulb tube). Solidified after distillation.

M.p.: 102° C. (not recrystallized).

Example 28

Ethyl 4-hydroxy-7-fluoro-indan-2-carboxylate

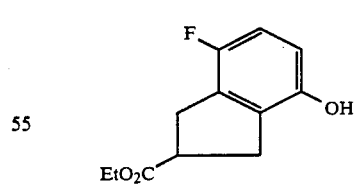

94 g (0.4 mol) of the compound from Example 26 are hydrogenated in 600 ml of ethanol using 20 g of Pd-C (5% strength) at 30 bar of H₂ and 60° C. for 4 h. The catalyst is filtered off, the solution is evaporated and the residue is flash chromatographed on silica gel (eluent: petroleum ether/acetone 5:1). After evaporating the fractions containing the product, the residue is recrystallized from ligroin.

Yield: 50.22 g (56.8% of theory).

M.p.: 103° C.

Example 29

Ethyl 4-hydroxy-indan-2-carboxylate

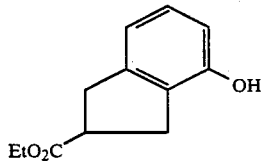

In analogy to the procedure of Example 28, the title compound was prepared from the indanone of Example 27.

Yield: 69.1%.

$^1$H-NMR (CDCl$_3$): δ=1.3 (t, 3H); 3.15–3.4 (m, 5H); 4.2 (q, 2H); 6.6 (d, 1H); 6.8 (d, 1H); 7.0 (t, 1H).

Example 30

(7-Methoxy-indan-1-on-2-yl)acetic acid

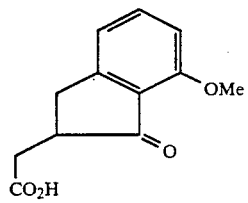

117 g (0.5 mol) of ethyl 7-methoxy-indan-1-one-2-carboxylate [cf. H. Immer, J. F. Bagli, J. Org. Chem. 33 (6), 1968, 2457–2462] in 100 ml of absolute ethanol are added dropwise to a sodium ethoxide solution formed from 11.5 g (0.5 mol) of sodium and 250 ml of absolute ethanol. 87.7 g (0.53 mol) of ethyl bromoacetate are then added dropwise to the hot solution and the mixture is heated to reflux until the solution has a neutral reaction (3 h). The solution is evaporated, ice water is added to the residue and the mixture is shaken 3 times with ether. The combined ester phases are washed with saturated NaCl and evaporated. The residue is refluxed in 370 ml of 20% strength HCl solution for 5 h and, after cooling, is shaken 3 times with 100 ml of CH$_2$Cl$_2$ each time. The combined CH$_2$Cl$_2$ phases are shaken twice with 200 ml of 10% strength NaOH solution each time, the combined NaOH solutions are brought to pH 1–2 using concentrated hydrochloric acid with ice cooling and shaken twice with 200 ml of CH$_2$Cl$_2$ each time. After drying over Na$_2$SO$_4$, the methylene chloride is distilled off and the residue is dried in vacuo.

Yield: 63.47 g (57.7% of theory).

$^1$H-NMR (CDCl$_3$): d=2.6 (q, 1H); 2.85 (dd, 1H); 3.0 (m, 2H); 3.4 (q, 1H); 3.95 (s, 3H); 6.8 (d, 1H); 7.0 (d, 1H); 7.55 (t, 1H).

Example 31

(4-Fluoro-7-hydroxy-indan-1-on-2-yl)acetic acid

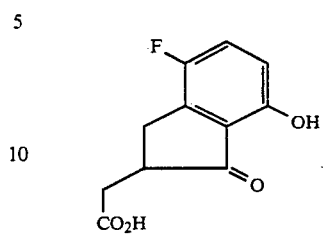

In analogy to the procedure of Example 30, the title compound was prepared from the 4-fluoro-indanone of Example 26 using double the amount of sodium methoxide.

Yield: 42%.

$^1$H-NMR (CDCl$_3$): δ=2.7 (q, 1H); 2.9 (m, 3H); 3.05 (m, 1H); 3.45 (q, 1H); 6.75 (dd, 1H); 7.2 (q, 1H); 8.8 (broad, 1H).

Example 32

(4-Methoxy-indan-2-yl)acetic acid

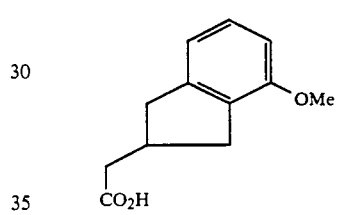

Zinc amalgam is prepared from 205 g of zinc turnings, 24.6 g of mercury(II) chloride, 306 ml of H$_2$O and 10 ml of concentrated hydrochloric acid by shaking for 10 minutes. It is decanted off and 19.6 g (89 mmol) of indanone from Example 30, dissolved in 178 ml of toluene, 223 ml of H$_2$O, 20 ml of glacial acetic acid and 400 ml of concentrated hydrochloric acid are added to the amalgam. The mixture is heated to reflux for 18 h, 400 ml of concentrated hydrochloric acid being added every 6 h. After cooling, the mixture is shaken 3 times using 300 ml of toluene each time, and the combined toluene phases are washed with saturated NaCl solution, dried over Na$_2$SO$_4$ and evaporated. The residue is flash chromatographed on silica gel (eluent: CH$_2$Cl$_2$/MeOH 10:1).

Yield: 13.7 g (74.6% of theory).

R$_f$=0.65 (CH$_2$Cl$_2$/MeOH 10:1).

Example 33

(4-Fluoro-7-hydroxy-indan-2-yl)acetic acid

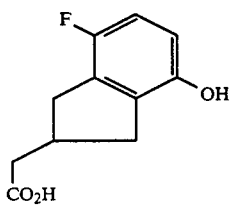

In analogy to the procedure of Example 32, the title compound was prepared from the 4-fluoro-indanone of Example 31.

Yield: 52.1%.

$R_f$=0.53 (CH$_2$Cl$_2$/MeOH 10:1).

Example 34

Ethyl (4-hydroxy-indan-2-yl)-acetate

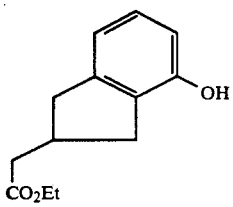

21.4 ml of boron tribromide, dissolved in 214 ml of absolute CH$_2$Cl$_2$, are added dropwise at −78° C. to 21.94 g (0.107 mol) of the compound from Example 32 in 214 ml of absolute CH$_2$Cl$_2$ and the mixture is stirred for 30 minutes. It is allowed to come to 20° C., stirred for 3 h, cooled again to −78° C. and 320 ml of methanol are added dropwise. The mixture is evaporated, and the residue is partitioned between 200 ml of CH$_2$Cl$_2$ and 200 ml of H$_2$O and the phases are separated. The organic phase is shaken 3 times with 100 ml of 10% strength NaOH solution each time, and the combined NaOH phases are brought to pH 1-2using concentrated hydrochloric acid with ice cooling and shaken twice with 150 ml of ethyl acetate each time. After drying over Na$_2$SO$_4$, the solution is evaporated and the residue is dried in vacuo. The residue is dissolved in 107 ml of absolute ethanol, dry hydrogen chloride is introduced until the solution is saturated and the mixture is refluxed for 2 h. After cooling, it is evaporated, and the residue is taken up in 100 ml of CH$_2$Cl$_2$ and washed with saturated Na$_2$CO$_3$ solution until neutral. After drying over Na$_2$SO$_4$, the solution is evaporated and the residue is flash chromatographed (eluent: CH$_2$Cl$_2$/acetone 40:1).

Yield: 15.25 g (65.1% of theory).

$R_f$=0.48 (CH$_2$Cl$_2$/acetone 20:1).

Example 35

Ethyl (4-fluoro-7-hydroxy-indan-2-yl)-acetate

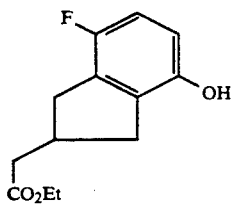

The title compound was prepared in analogy to the procedure of Example 34 by esterification of the compound from Example 33 in ethanolic hydrochloric acid solution.

Yield: 86.7%.

$^1$H-NMR (CDCl$_3$): d=1.25 (t, 3H); 2.5-2.7 (m, 4H); 2.95 (h, 1H); 3.35-3.45 (m, 2H); 4.15 (q, 2H); 5.8 (s, 1H); 6.7 (dd, 1H); 7.05 (m, 1H).

Example 36

Ethyl 8-(2-cyanoethyl-1-oxy)tetralin-2-carboxylate

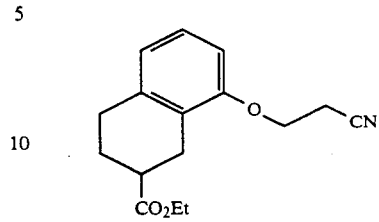

44.63 g (0.202 mol) of ethyl 8-hydroxy-tetralin-2-carboxylate [obtained from the esterification of the known carboxylic acid; D. W. Johnson, L. N. Mander, Aust. J. Chem. 27 (6), 1974, 1277–1286]and 114 g (2.15 mol) of acrylonitrile are refluxed with 5.9 ml of 40% methanolic Triton B solution for 24 h with vigorous stirring. After cooling, a 2.5-fold volume of ether is added, the mixture is shaken 3 times with 200 ml of 10% strength NaOH solution each time, and the ether phase is dried over Na$_2$SO$_4$ and evaporated. The residue is flash chromatographed on silica gel (eluent: CH$_2$Cl$_2$/acetone 40:1).

Yield: 40.15 g (72.5% of theory) of oil.

$R_f$=0.57 (CH$_2$Cl$_2$/acetone 40:1).

The compounds shown in Table 4 were prepared in analogy to the procedure of Example 36:

TABLE 4

| Example No. | Structure | M.p./$R_f$ value |
|---|---|---|
| 37 | 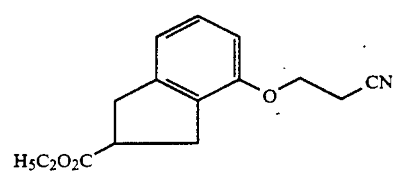 | 55–57° C. |
| 38 | 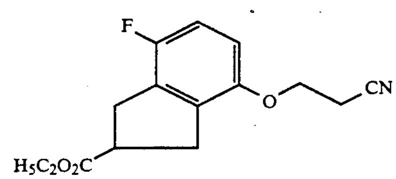 | 48–50° C. |
| 39 | 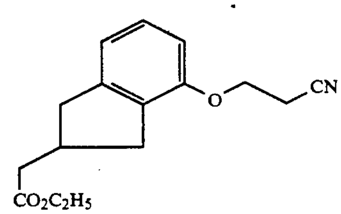 | 0.56 (CH$_2$Cl$_2$/acetone 40:1) |
| 40 | 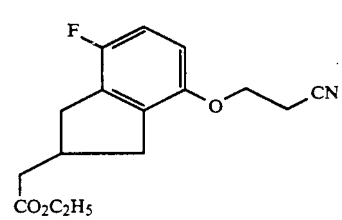 | 0.52 (CH$_2$Cl$_2$/acetone 40:1) |

Example 41

Ethyl 4-oxo-7,8,9,10-tetrahydro-naphtho[1,2-b]pyran-9-carboxylate

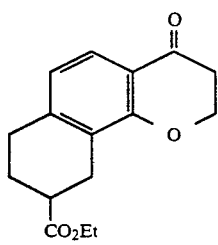

39.19 g (0.144 mol) of the compound from Example 36 are stirred at 50° C. for 10 h in 216 ml of HF. The mixture is evaporated, the residue is taken up in 100 ml of $CH_2Cl_2$ and the solution is washed with saturated $Na_2CO_3$ solution until neutral. After drying over $Na_2SO_4$, the solution is evaporated and the residue is flash chromatographed on silica gel (eluent: $CH_2Cl_2$/acetone 40:1).

Yield: 25.98 g (66.1% of theory).

$R_f$=0.51 ($CH_2Cl_2$/acetone 40:1).

The compounds shown in Table 5 were prepared in analogy to the procedure of Example 41:

TABLE 5

| Example No. | Structure | M.p./$R_f$ value |
|---|---|---|
| 42 | 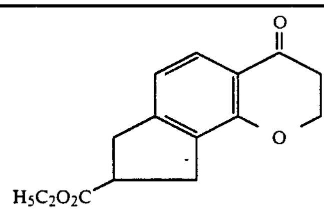 | 57° C. |
| 43 | 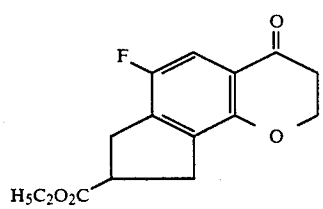 | 0.24 (petroleum ether/acetone 3:1) |
| 44 | 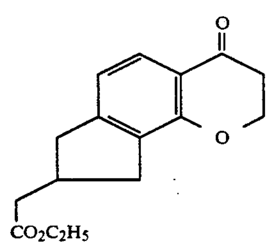 | 59–61° C. |
| 45 | 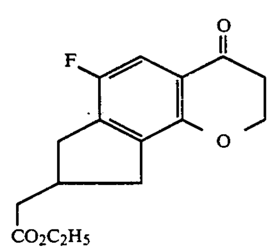 | |

Example 46

Ethyl 7-(2-propinyloxy)-2,3-dihydro-benzofuran-2-carboxylate

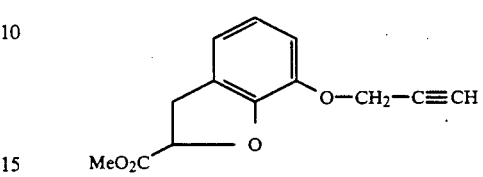

37.57 g (0.194 mol) of methyl 7-hydroxy-2,3-dihydro-benzofuran-2-carboxylate [prepared from the known 7-methoxy-2,3-dihydro-benzofuran-2-carboxylic acid, G. Goldenberg et al., Chim. Ther. 8 (3), 1973, 259–270] and 32.85 g (0.213 mol) of propargyl bromide (80% in toluene) are refluxed in the presence of 29.49 g (0.213 mol) of $K_2CO_3$ in 194 ml of dry butanone for 5 h. After cooling, the precipitate is filtered off and washed well with acetone, and the filtrate is evaporated. The residue is taken up in 200 ml of $CH_2Cl_2$, shaken twice with 10% strength NaOH solution, dried over $Na_2SO_4$ and evaporated. The residue is flash chromatographed on silica gel (eluent: petroleum ether/acetone 5:1).

Yield: 38.21 g (85.0% of theory).

M.p.: 54° C. (after chromatography, not recrystallized).

Example 47

Methyl 7-(3-bromo-2-propinyloxy)-2,3-dihydro-benzofuran-2-carboxylate

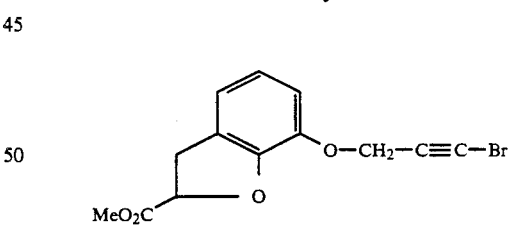

67.98 g (0.293 mol) of the compound from Example 46 and 61 g (0.340 mol) of NBS are stirred at 20° C. for 30 minutes in the presence of 5 g of $AgNO_3$ in 2.5 l of acetone. The mixture is concentrated to about 500 ml, poured onto 2 l of ice/water and shaken twice with 500 ml of ethyl acetate each time. The mixture is filtered, and the ethyl acetate phases are dried over $Na_2SO_4$ and evaporated. The residue is flash chromatographed on silica gel (eluent: petroleum ether/acetone 3:1).

Yield: 87.47 g (96% of theory).

$R_f$=0.42 (petroleum ether/acetone 3:1).

Example 48

Methyl 6-oxo-2,3,6,7-tetrahydro-8H-furo[3,2-h][1]-benzopyran-2-carboxylate

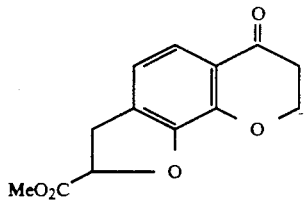

91 g (292.6 mmol) of the compound from Example 47 and 125 g (292.6 mmol) of mercury(II) trifluoroacetate are combined in 293 ml of trifluoroacetic acid (exothermic!) and refluxed for 4 h. The solution is concentrated, 500 ml of $CH_2Cl_2$ are added and the mixture is washed with saturated sodium carbonate solution until neutral. After drying over $Na_2SO_4$, the solution is filtered off and evaporated, and the residue is flash chromatographed on silica gel (eluent: $CH_2Cl_2$/acetone 10:1).

Yield: 18.52 g (25.5% of theory).

M.p.: 108° C. (after chromatography, not recrystallized).

Example 49

Ethyl-(1,2,5,6,7,8-hexahydro-4-cyano-10-phenanthryl)-carboxylate

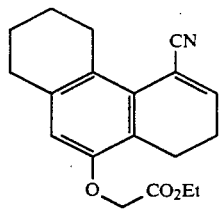

2-3 drops of $BF_3$ etherate are added to 21.84 g (72.2 mmol) of the compound from Example 9 and 21.5 g (217 mmol) of trimethylsilyl cyanide and the mixture is stirred at 20° C. until the carbonyl band at 1690 cm$^{-1}$ in the IR has disappeared (about 15 minutes). 72.3 ml of trifluoroacetic acid are added cautiously (evolution of HCN) and the mixture is heated to reflux for 2 h. After cooling, it is concentrated and the residue is dissolved in 200 ml of $CH_2Cl_2$ and washed with saturated $Na_2CO_3$ solution until neutral. After drying over $Na_2SO_4$, the solution is evaporated and the residue is flash chromatographed on kieselguhr (eluent: petroleum ether/acetone 3:1).

Yield: 15.81 g (70.3% of theory).

M.p.: 77° C. (after chromatography, not recrystallized).

The compounds shown in Table 6 were prepared in analogy to the procedure of Example 49.

TABLE 6

| Example No. | Structure | M.p./$R_f$ value |
|---|---|---|
| 50 | 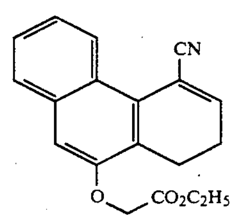 | 105° C. |
| 51 | 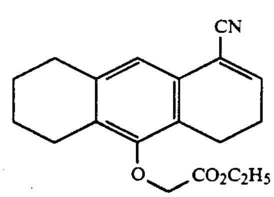 | |
| 52 | 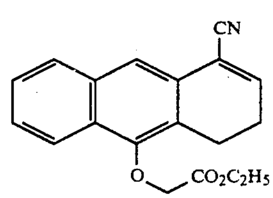 | 76–79° C. |
| 53 | 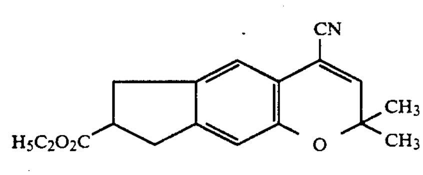 | 96° C. |

TABLE 6-continued

| Example No. | Structure | M.p./$R_f$ value |
|---|---|---|
| 54 | (structure) | 64° C. |
| 55 | (structure) | 95° C. |
| 56 | (structure) | 83° C. |
| 57 | (structure) | 120° C. |
| 58 | (structure) | 72° C. |
| 59 | (structure) | 58° C. |
| 60 | (structure) | 0.19 (petroleum ether/acetone 3:1) |

TABLE 6-continued

| Example No. | Structure | M.p./$R_f$ value |
|---|---|---|
| 61 | 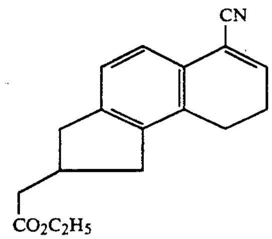 | 0.5 ($CH_2Cl_2$) |
| 62 | 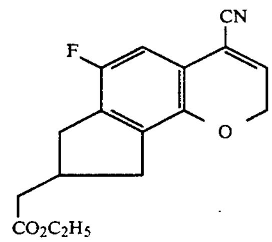 | |
| 63 | 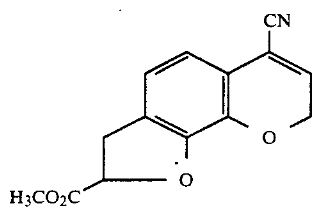 | 113° C. |

Example 64

(1,2,5,6,7,8-Octahydro-4-aminomethyl-10phenanthryl-)oxyacetamide

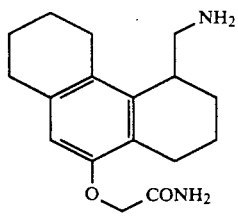

27.09 g (87.1 mmol) of the compound from Example 49 are hydrogenated on the double bond in 250 ml of THF in the presence of 3 g of Pd-C (54% strength) at 50° C. and 9 bar of $H_2$ until completion of hydrogen uptake (1-3 h). After cooling, the catalyst is filtered off, and 100 ml of liquid ammonia and 8 g of Ra-Ni are added to the THF solution. The mixture is then hydrogenated again at 90 bar of $H_2$ and 70° C. until completion of hydrogen uptake (3-6 h). After cooling, the catalyst is filtered off, the solution is evaporated and the residue is flash chromatographed on silica gel (eluent: $CH_2Cl_2$/MeOH 10:1). With the ethylesters, however, aminolysis to the carboxamide does not always take place.

Yield: 15.33 g (61.1% of theory).

$^1$H-NMR ($CDCl_3$+DMSO-$d_6$): d=1.5-1.65 (m, 4H); 1.7-1.9 (m, 6H); 2.6-2.9 (m, 9H); 4.45 (s, 2H); 5.9 (broad, 1H); 6.4 (s, 1H); 6.55 (broad, 1H).

The compounds shown in Table 7 were prepared in analogy to the procedure of Example 64:

TABLE 7

| Example No. | Structure | M.p./$R_f$ value |
|---|---|---|
| 65 | 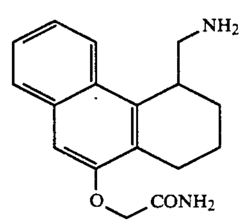 | |

TABLE 7-continued

| Example No. | Structure | M.p./R_f value |
|---|---|---|
| 66 | 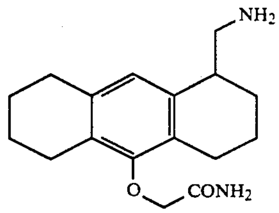 | |
| 67 | 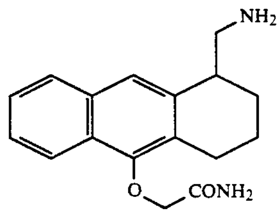 | |
| 68 | 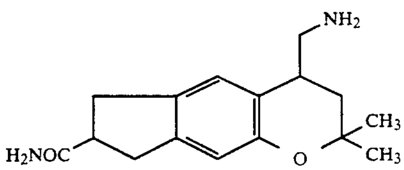 | |
| 69 | 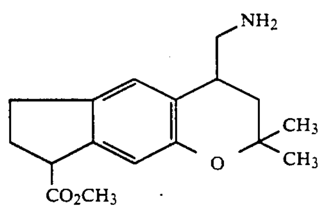 | |
| 70 | 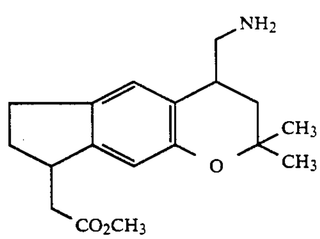 | |
| 71 | 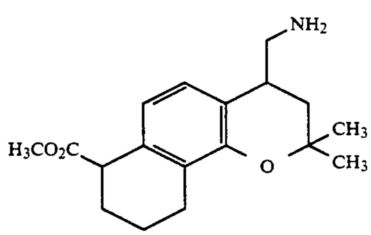 | |
| 72 | 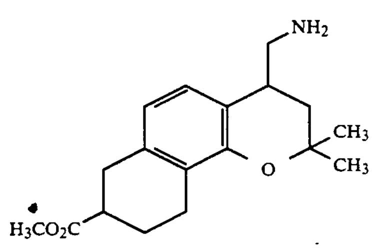 | |

TABLE 7-continued

| Example No. | Structure | M.p./$R_f$ value |
|---|---|---|
| 73 | (structure) | |
| 74 | (structure) | |
| 75 | (structure) | |
| 76 | (structure) | 0.1 (CH$_2$Cl$_2$/MeOH 10:1) |
| 77 | (structure) | |
| 78 | (structure) | 50–55° C. |

B) PREPARATION EXAMPLES (FORMULA I)

General procedure 10 ml of the amine (see Examples 64-78) are refluxed in 20 ml of absolute THF together with 10 ml of the corresponding sulphonyl chloride and 25 mmol of anhydrous potassium carbonate until the reaction is complete (TLC checking, 6-24 h). The mixture is evaporated, and the residue is partitioned between 50 ml of ethyl acetate and 100 ml of 1N HCl solution and stirred until all solids are dissolved. After phase separation, the ethyl acetate phase is shaken once each with 1N HCl, saturated NaHCO₃ solution and saturated NaCl solution, dried over Na₂SO₄ and evaporated. If required, the residue can be further purified by flash chromatography. The residue is dissolved in 30 ml of methanol and 10 ml of 3N KOH solution are added. If esters are present, the mixture is stirred at room temperature for 2-4 h, and in the case of amides it is refluxed for 6-8 h. The methanol is evaporated off, and the KOH phase is washed with methylene chloride and brought to pH 1-2 using concentrated HCl solution with ice cooling. Products obtained as solids are filtered off, and with oily products the mixture is extracted twice with ethyl acetate. After drying in a high vacuum, the compounds are pure. The compounds are compiled in the following tables.

The complete $^1$H-NMR spectra are in each case only indicated once for each basic structure. After this, only the signals of the different benzenesulphonamide groups are indicated. In order to distinguish the final products, the example numbers are additionally provided with the Roman numeral I (corresponds to general formula I).

TABLE I

| Ex. No. | $R^{11}$ | Yield (%) | M.p.: (°C.) | $^1$H-NMR data (CDCl₃) |
|---|---|---|---|---|
| 1 (I) | F | 73.2 | 169-170 (not recrystallized) | |
| 2 (I) | Cl | 76.4 | | 7.5 (d, 2H); 7.75 (d, 2H) |
| 3 (I) | H | 62.3 | | 7.5-7.7 (m, 3H); 7.85-8.0 (m, 2H) |
| 4 (I) | CF₃ | 66.1 | | 7.75 (d, H); 8.0 (d, 2H) |
| 5 (I) | C(CH₃)₃ | 84.9 | | 1.35 (s, 9H); 7.5 (d, 2H) |
| 6 (I) | CH₃ | 76.3 | | 2.45 (s, 3H); 7.35 (d, 2H) |

TABLE II

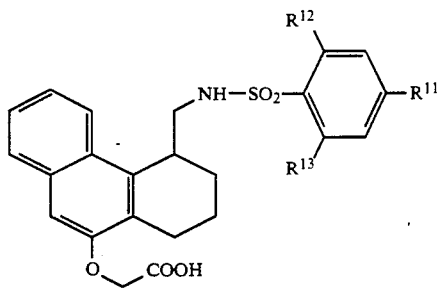

| Example No. | $R^{11}$ | $R^{12}$ | $R^{13}$ | Yield (%) | $^1$H-NMR data (CDCl₃) |
|---|---|---|---|---|---|
| 7 (I) | F | H | H | 46.4 | 1.65-1.9 (m, 3H); 2.25 (d, 1H); 2.6-2.75 (m, 1H); 2.95-3.1 (m, 2H); 3.15-3.25 (m, 1H); 3.65 (pseudo d, 1H); 4.7 (s, 2H); 6.84 (s, 1H); 6.9 (t, 1H); 7.1 (pseudo t, 2H); 7.3-7.4 (m, 2H); 7.6-7.65 (m, 1H); 7.85-7.9 (m, 2H); 7.95 (d, 1H) |
| 8 (I) | Cl | H | H | 73.2 | 7.5 (d, 2H); 7.75 (d, 2H) |
| 9 (I) | OCF₃ | H | H | 60.1 | 7.35 (d, 2H); 7.9 (d, 2H) |
| 10 (I) | H | Cl | Cl | 37.7 | 7.05 (t, 1H); 7.2 (pseudo-d, 2H) |
| 11 (I) | CN | H | H | 73.3 | 7.5 (d, 2H); 7.7 (d, 2H) |

TABLE III

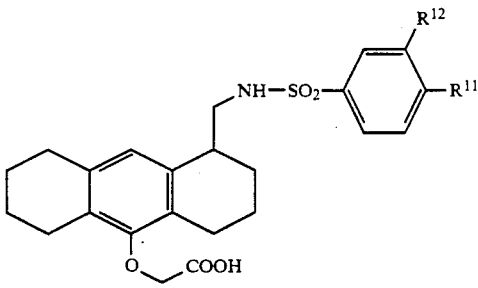

| Example No. | $R^{11}$ | $R^{12}$ | Yield (%) | Melting point (°C.) | $^1$H-NMR data (CDCl₃) |
|---|---|---|---|---|---|
| 12 (I) | F | H | 66.1 | 140-144 (not recrystallized) | |
| 13 (I) | Cl | H | 61.2 | | 7.55 (d, 2H); 7.8 (d, 2H); 8.0 (m, 2H) |
| 14 (I) | H | H | 76.2 | | 7.5-7.7 (m, 3H); 7.85-8.0 (m, 2H) |
| 15 (I) | CF₃ | H | 67.3 | | 7.75 (d, 2H); 8.0 (d, 2H) |
| 16 (I) | Cl | CF₃ | 59.3 | | 7.6 (d, 1H); 7.95 (dd, H); 8.2 (s, 1H) |
| 17 (I) | OCH₃ | H | 72.9 | | 3.8 (s, 3H); 7.05 (d, 2H); 7.55 (d, 2H) |
| 18 (I) | CH₃ | H | 71.0 | | 2.45 (s, 3H); 7.35 (d, 2H); 7.7 (d, 2H) |

TABLE IV

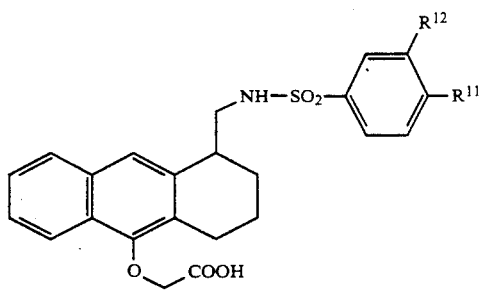

| Example No. | R[11] | R[12] | Yield (%) | Melting point (°C.) | $^1$H-NMR data (CDCl$_3$) |
|---|---|---|---|---|---|
| 19 (I) | F | H | 83.2 | | |
| 20 (I) | Cl | H | 62.1 | | 7.45 (d, 2H); 7.75 (d, 2H) |
| 21 (I) | H | H | 69.3 | | 7.5–7.7 (m, 3H); 7.85–8.0 (m, 2H) |
| 22 (I) | CF$_3$ | H | 51.7 | | 7.75 (d, 2H); 8.0 (d, 2H) |
| 23 (I) | Cl | CF$_3$ | 38.3 | | 7.6 (d, 1H); 7.95 (dd, 1H); 8.25 (s, 1H) |
| 24 (I) | C(CH$_3$)$_3$ | H | 66.3 | | |
| 25 (I) | CH$_3$ | H | 64.8 | | |
| 26 (I) | Cl | Cl | 71.5 | | |

TABLE V

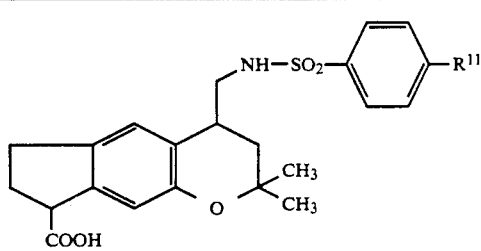

| Example No. | R[11] | Yield (%) | Melting point (°C.) | $^1$H-NMR data (CDCl$_3$) |
|---|---|---|---|---|
| 27 (I) | H | 46.8 | | |
| 28 (I) | F | 32.1 | | 7.2 (t, 2H); 7.8–7.85 (m, 2H) |
| 29 (I) | Cl | 72.7 | | |

TABLE VI

| Example No. | R[11] | Yield (%) | Melting point (°C.) | $^1$H-NMR data (CDCl$_3$) |
|---|---|---|---|---|
| 30 (I) | H | 62.6 | | |
| 31 (I) | F | 89.2 | | 7.2 (t, 2H); 7.85–7.9 (m, 2H) |
| 32 (I) | Cl | 81.5 | | |

TABLE VII

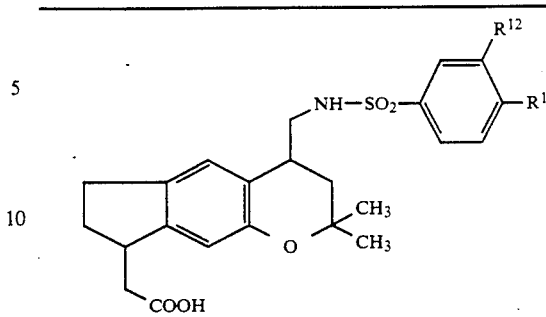

| Example No. | R[11] | R[12] | Yield (%) | Melting point (°C.) | $^1$H-NMR data (CDCl$_3$) |
|---|---|---|---|---|---|
| 33 (I) | H | H | 92.5 | | |
| 34 (I) | F | H | 78.4 | | 7.2 (t, 2H); 7.85–7.9 (m, 2H) |
| 35 (I) | Cl | H | 87.7 | | 7.55 (dd, 2H); 7.8 (dd, 2H) |
| 36 (I) | O—C$_6$H$_5$ | H | 56.3 | | |
| 37 (I) | NO$_2$ | H | 56.7 | | |
| 38 (I) | Cl | Cl | 78.1 | | |

TABLE VIII

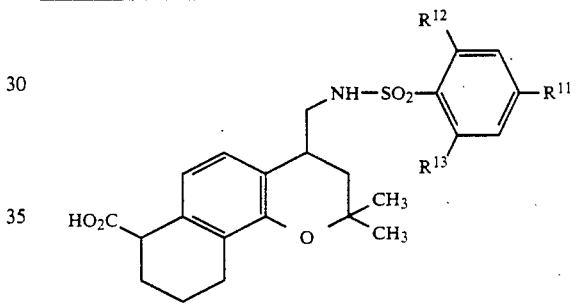

| Example No. | R[11] | R[12] | R[13] | Yield (%) | $^1$H-NMR data (CDCl$_3$) |
|---|---|---|---|---|---|
| 39 (I) | H | H | H | 62.9 | |
| 40 (I) | F | H | H | 87.6 | 7.2 (t, 2h); 7.85–7.9 (m, 2H) |
| 41 (I) | Cl | H | H | 93.0 | 7.55 (dd, 2H); 2.8 (d, 2H) |
| 42 (I) | H | Cl | CH$_3$ | 82.9 | |
| 43 (I) | OCH$_3$ | H | H | 69.6 | |

TABLE IX

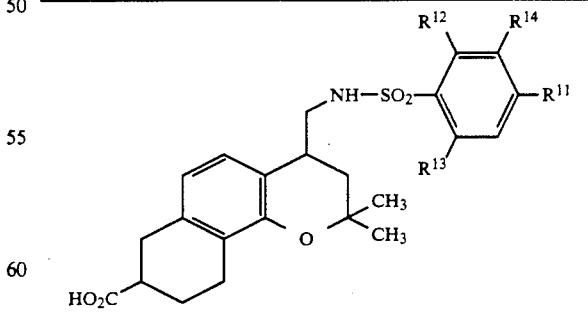

| Example No. | R[11] | R[12] | R[13] | R[14] | Yield (%) | $^1$H-NMR data (CDCl$_3$) |
|---|---|---|---|---|---|---|
| 44 (I) | H | H | H | H | 72.3 | |
| 45 (I) | F | H | H | H | 76.9 | 7.25 (t, 2H); 7.85–7.9 (m, 2H) |
| 46 (I) | Cl | H | H | H | 64.2 | |

TABLE IX-continued

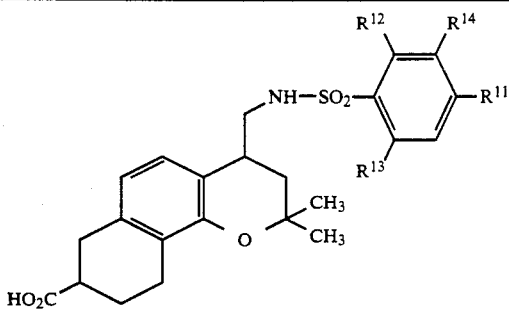

| Example No. | $R^{11}$ | $R^{12}$ | $R^{13}$ | $R^{14}$ | Yield (%) | $^1$H-NMR data (CDCl$_3$) |
|---|---|---|---|---|---|---|
| 47 (I) | OCF$_3$ | H | H | H | 71.0 | 7.35 (d, 2H); 7.9 (d, 2H) |
| 48 (I) | CF$_3$ | H | H | H | 56.3 | |
| 49 (I) | H | Cl | Cl | H | 49.2 | |
| 50 (I) | C(CH$_3$)$_3$ | H | H | H | 76.3 | |
| 51 (I) | CN | H | H | H | 69.6 | |
| 52 (I) | Cl | H | H | Cl | 69.3 | 7.5–7.7 (m, 2H); 7.9 (d, 1H) |

TABLE X

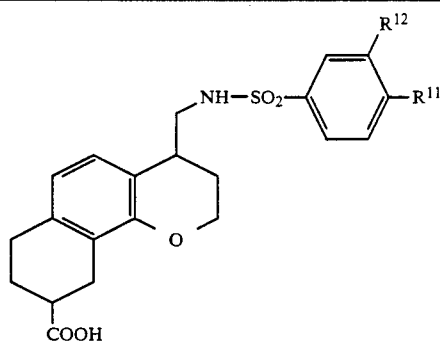

| Example No. | $R^{11}$ | $R^{12}$ | Yield (%) | Melting point (°C.) R$_f$ values (methylene chloride/methanol 10:1) |
|---|---|---|---|---|
| 53 (I) | H | H | 68.2 | |
| 54 (I) | F | H | 66.3 | 0.53 |
| 55 (I) | Cl | H | 70.7 | 0.56 |
| 56 (I) | CF$_3$ | H | 63.5 | 140 (not recrystallized) |
| 57 (I) | OCHF$_2$ | H | 36.4 | 185 (not recrystallized) |
| 58 (I) | Cl | CF$_3$ | 65.3 | |
| 59 (I) | CN | H | 76.3 | |
| 60 (I) | OCH$_3$ | H | 74.3 | |
| 61 (I) | CH$_3$ | H | 59.9 | |

TABLE XI

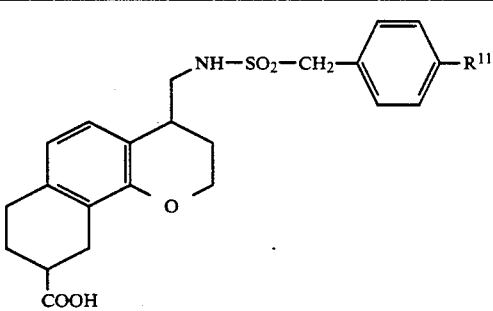

| Example No. | $R^{11}$ | Yield (%) |
|---|---|---|

TABLE XI-continued

| 62 | CF$_3$ | 72.0 |
|---|---|---|

TABLE XII

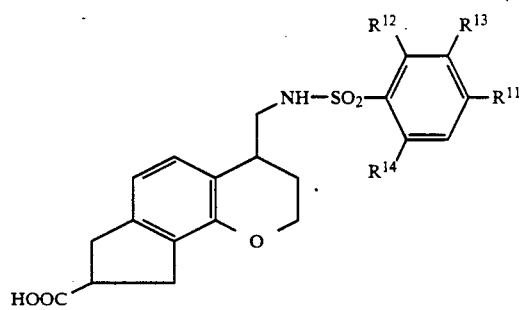

| Example No. | $R^{11}$ | $R^{12}$ | $R^{13}$ | $R^{14}$ | Yield (%) | M.p. (°C.) |
|---|---|---|---|---|---|---|
| 63 (I) | H | H | H | H | 66.6 | |
| 64 (I) | Cl | H | H | H | 70.5 | |
| 65 (I) | F | H | H | H | 56.6 | 133–136 (not recrystallized) |
| 66 (I) | CF$_3$ | H | H | H | 60.3 | |
| 67 (I) | H | Cl | H | Cl | 63.1 | |
| 68 (I) | Cl | CF$_3$ | H | H | 62.6 | |
| 69 (I) | C(CH$_3$)$_3$ | H | H | H | 79.3 | |
| 70 (I) | Cl | H | Cl | H | 67.6 | |
| 71 (I) | CH$_3$ | H | H | | 49.1 | |

TABLE XIII

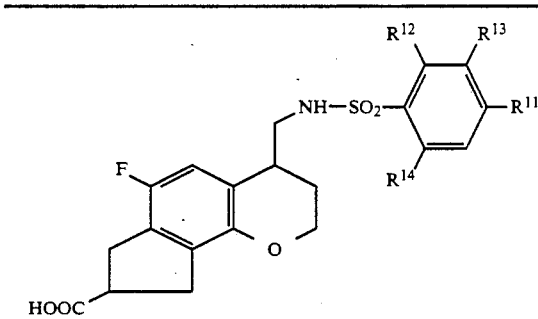

| Example No. | $R^{11}$ | $R^{12}$ | $R^{13}$ | $R^{14}$ | Yield (%) | Melting point (°C.)/R$_f$ values (methylene chloride/methanol (10:1) |
|---|---|---|---|---|---|---|
| 72 (I) | H | H | H | H | 58.9 | |
| 73 (I) | F | H | H | H | 60.1 | 84–85 |
| 74 (I) | Cl | H | H | H | 74.2 | 70 |
| 75 (I) | CF$_3$ | H | H | H | 39.4 | 75 |
| 76 (I) | OCF$_3$ | H | H | H | 39.6 | 0.36 |
| 77 (I) | H | Cl | H | Cl | 54.1 | |
| 78 (I) | Cl | H | CF$_3$ | H | 41.1 | |
| 79 (I) | H | Cl | H | CH$_3$ | 43.8 | |
| 80 (I) | C(CH$_3$)$_3$ | H | H | H | 60.1 | |
| 81 (I) | CN | H | H | H | 49.6 | |
| 82 (I) | NO$_2$ | H | H | H | 74.3 | |
| 83 (I) | OCH$_3$ | H | H | H | 55.0 | |
| 84 (I) | CH$_3$ | H | H | H | 53.9 | |
| 85 (I) | Cl | H | Cl | H | 58.6 | |

TABLE XIV

[Structure shown with R¹², R¹¹, R¹³ substituents on phenylsulfonamide connected to chroman with COOH]

| Example No. | R¹¹ | R¹² | R¹³ | Yield (%) | R_f values (methylene chloride/methanol (10:1) |
|---|---|---|---|---|---|
| 86 (I) | H | H | H | 73.5 | |
| 87 (I) | F | H | H | 65.2 | 0.58 |
| 88 (I) | Cl | H | H | 47.3 | 0.61 |
| 89 (I) | H | Cl | Cl | 65.4 | |
| 90 (I) | CF₃ | H | H | 54.0 | |

TABLE XV

[Structure with F on ring]

| Example No. | R¹¹ | Yield (%) | ¹H-NMR data (CDCl₃) |
|---|---|---|---|
| 91 (I) | H | 60.6 | |
| 92 (I) | F | 86.3 | 7.2 (t, 2H); 7.85–7.9 (m, 2H) |
| 93 (I) | Cl | 79.8 | |

TABLE XVI

[Structure with HOOC]

| Example No. | R¹¹ | Yield (%) | R_f value (methylene chloride/methanol 5:1) |
|---|---|---|---|
| 94 (I) | H | 52.3 | |
| 95 (I) | F | 40.2 | 0.66 |
| 96 (I) | Cl | 55.1 | 0.67 |
| 97 (I) | CF₃ | 63.1 | 0.63 |

It is understood that the specification and examples are illustrative but not limitative of the present invention and that other embodiments within the spirit and scope of the invention will suggest themselves to those skilled in the art.

We claim:

1. A phenylsulphonamide of the formula

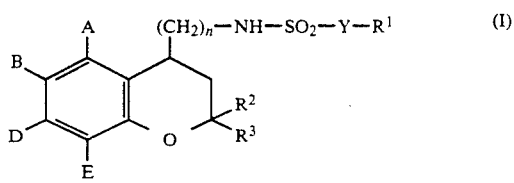

in which

A, B, D and E are identical or different and
represent hydrogen, hydroxyl, halogen, trifluoromethyl, trifluoromethoxy, straight-chain or branched alkyl or alkoxy in each case having up to 8 carbon atoms, or
represent aryl having 6 to 10 carbon atoms, which is optionally monosubstituted to trisubstituted by identical or different substituents from the group consisting of halogen, trifluoromethyl, trifluoromethoxy, carboxyl, nitro, cyano and straight-chain or branched alkyl, alkoxy or alkoxycarbonyl in each case having up to 8 carbon atoms, or
represent a group of the formula —(CH₂)$_m$—CO—Z or —O—(CH₂)$_p$—CO—Z, wherein
m—denotes a number 0, 1, 2, 3 or 4,
p—denotes a number 1, 2, 3 o 4, and
Z—denotes hydroxyl, straight-chain or branched alkoxy having up to 8 carbon atoms, aryloxy having 6 to 10 carbon atoms or a group of the formula —NR⁴R⁵, wherein R⁴ and R⁵ are identical or different and denote hydrogen, straight-chain or branched alkyl having up to 8 carbon atoms or aryl having 6 to 10 carbon atoms, with the proviso that either A and B or B and D or D and E together must form a 5- to 7-membered saturated or unsaturated carbocycle fused to the basic structure and which in turn may be substituted by a group of the formula —(CH₂)$_m$—CO—Z or —O—(CH₂)$_p$—CO—Z, Y—represents the group—(CH₂)$_s$—, wherein s—denotes a number 0, 1, 2, 3 or 4, R¹—represents aryl having 6 to 10 carbon atoms, which is optionally monosubstituted to pentasubstituted by identical or different substituents from the group consisting of halogen, cyano, nitro, trifluoromethyl, difluoromethyl, difluoromethoxy, trifluoromethoxy, carboxyl, aryloxy having 6 to 10 carbon atoms, straight-chain or branched alkyl, alkoxy or alkoxycarbonyl in each case having up to 8 carbon atoms and —NR⁴R⁵, n—represents a number 0, 1 or 2, and R² and R³ are identical or different and represent hydrogen of straight-chain or branched alkyl having up to 8 carbon atoms, or a salt thereof.

2. A phenylsulphonamide according to claim 1, wherein

A, B, D and E are identical or different and
represent hydrogen, hydroxyl, fluorine, chlorine, bromine, trifluoromethyl, trifluoromethoxy, straight-chain or branched alkyl or alkoxy in each case having up to 6 carbon atoms, or
represent a group of the formula —(CH₂)$_m$—CO—Z or —O—(CH₂)$_p$—CO—Z, wherein m—denotes a number 0, 1, 2 or 3, p—denotes a number 1, 2 or 3, and Z—denotes hydroxyl, straight-chain or branched alkoxy having up to 6 carbon atoms or phenoxy, with the proviso that either A and B or B and D or D and E together form a cyclopentano, cyclohexano or benzo ring fused to the basic structure, which may in turn be substituted by a group of the formula —(CH$_2$)$_m$—CO—Z or —O—(CH$_2$)$_p$—CO—Z Y—represents the group —(CH$_2$)$_s$, wherein s—denotes a number 0, 1, 2 or 3, R$^1$—represents phenyl which is optionally monosubstituted to tetrasubstituted by identical or different substituents from the group consisting of phenoxy, fluorine, chlorine, bromine, iodine, cyano, nitro, trifluoromethyl, trifluoromethoxy, difluoromethoxy, difluoromethyl, carboxyl and straight-chain or branched alkyl or alkoxy in each case having up to 6 carbon atoms, n—represents a number 0 or 1, R$^2$ and R$^3$ are identical or different and represent hydrogen or straight-chain or branched alkyl having up to 6 carbon atoms, or a salt thereof.

3. A phenylsulphonamide according to claim 1, wherein

A, B, D and E are identical or different and represent hydrogen, hydroxyl, fluorine, chlorine, trifluoromethyl or trifluoromethoxy, or represent a group of the formula —(CH$_2$)$_m$—CO—Z or —O—(CH$_2$)$_p$—CO—Z, wherein m—denotes a number 0, 1 or 2, p—denotes a number 1 or 2, and Z—denotes hydroxyl, straight-chain or branched alkoxy having up to 4 carbon atoms or phenoxy, with the proviso that either A and B or B and D or D and E together form a cyclopentano, cyclohexano or benzo ring fused to the basic structure, which may in turn be substituted by a group of the formula —(CH$_2$)$_m$—CO—Z or —O—(CH$_2$)$_p$—CO—Z, Y—represents the group —(CH$_2$)$_s$—, wherein s—denotes the number 0 or 1, R$^1$—represents phenyl which is optionally monosubstituted to trisubstituted by identical or different substituents from the group consisting of phenoxy, cyano, fluorine, chlorine, trifluoromethyl, trifluoromethoxy, difluoromethyl, difluoromethoxy, nitro, carboxyl and straight-chain or branched alkyl or alkoxy having up to 4 carbon atoms, n—represents the number 1, and R$^2$ and R$^3$ are identical or different and represent hydrogen or straight-chain or branched alkyl having up to 4 carbon atoms, or a salt thereof.

4. A compound according to claim 1, wherein such compound is 8-carboxy-5-(4-chlorophenyl-sulphonylaminomethyl)-2,3,8,9-tetrahydro-6H-cyclopenta-[h]-1-benzopyran of the formula

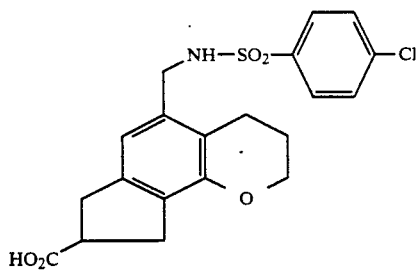

or a salt thereof.

5. A compound according to claim 1, wherein such compound is 8-carboxy-5-(4-fluorophenyl-sulphonylaminomethyl)-2,3,8,9-tetrahydro-6H-cyclopenta-[h]-1-benzopyran of the formula

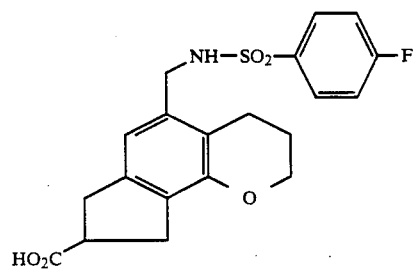

or a salt thereof.

6. A compound according to claim 1, wherein such compound is 8-carboxy-5-(4-fluorophenyl-sulphonylaminomethyl)-6-fluoro-2,3,8,9-tetrahydro-6H-cyclopenta-[h]-1-benzopyran of the formula

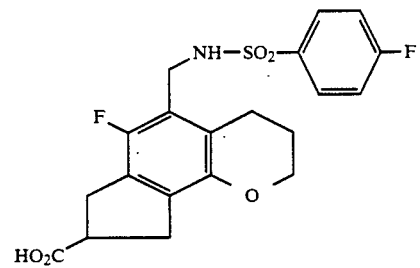

or a salt thereof.

7. A compound according to claim 1, wherein such compound is 8-carboxy-5-(4-chlorophenyl-sulphonylaminomethyl)-6-fluoro-2,3,8,9-tetrahydro-6H-cyclopenta-[h]-1-benzopyran of the formula

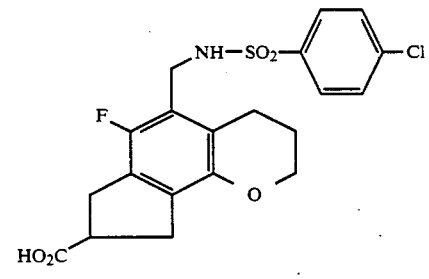

or a salt thereof.

* * * * *

UNITED STATES PATENT AND TRADEMARK OFFICE
CERTIFICATE OF CORRECTION

PATENT NO. : 5,191,092

DATED : March 2, 1993

INVENTOR(S) : Niewohner et al.

It is certified that error appears in the above-identified patent and that said Letters Patent is hereby corrected as shown below:

Title Page        [75] Inventors: 5th Inventor delete " Norma " and substitute -- Norman --

Col. 44, line 28    After " 3 " delete " o " and substitute -- or --

Signed and Sealed this

Seventeenth Day of May, 1994

*Attest:*

BRUCE LEHMAN

*Attesting Officer*      Commissioner of Patents and Trademarks